United States Patent
Mattalino et al.

(10) Patent No.: US 10,092,453 B2
(45) Date of Patent: Oct. 9, 2018

(54) PROTECTIVE HEAD COVERING WITH NECK SUPPORT FOR ANESTHETIZED PATIENT AND METHOD THEREFOR

(75) Inventors: Angelo J. Mattalino, Scottsdale, AZ (US); Laird L. Hatch, Cave Creek, AZ (US); Eric J. Church, Phoenix, AZ (US)

(73) Assignee: AEL Medical, LLC, Cave Creek, AZ (US)

( * ) Notice: Subject to any disclaimer, the term of this patent is extended or adjusted under 35 U.S.C. 154(b) by 1667 days.

(21) Appl. No.: 12/539,320

(22) Filed: Aug. 11, 2009

(65) Prior Publication Data

US 2011/0036358 A1    Feb. 17, 2011

(51) Int. Cl.
*A61F 11/00*    (2006.01)
*A61F 13/00*    (2006.01)
(Continued)

(52) U.S. Cl.
CPC ........ *A61F 13/00987* (2013.01); *A61B 46/00* (2016.02); *A61F 7/02* (2013.01);
(Continued)

(58) Field of Classification Search
CPC .. A61G 13/12; A61G 13/121; A61G 13/1205; A61G 7/07; A61G 13/126; A61G 13/127; A61G 13/1215; A61G 7/072; A47G 9/1063; A47G 9/10; A47G 9/1009; A47G 2009/1018; A47G 9/1081; A47G 9/1036; A47G 9/1054; A41D 31/11; A41D 13/1107; A41D 13/1161; A41D 13/1184; A42B 1/008; A61F 13/00987; A61F 7/02; A61F 2007/0225; A61F 2007/0228; A61F 2007/0233; A61F 13/00; A61F 13/00004; A61F 13/00008; A61F 13/00021; A61F 13/00029; A61F 13/00025; A61F 13/12; A61F 13/122; A61F 13/124; A61F 5/3707; A61F 13/126; A61F 13/128; A61F 2007/0054; A61F 7/00; A61F 2007/0001; A61F 2007/0002; A61F 2007/0003;
(Continued)

(56) References Cited

U.S. PATENT DOCUMENTS

3,075,521 A * 1/1963 Grassl .............................. 602/18
4,095,290 A * 6/1978 O'Brien .............................. 2/9
(Continued)

*Primary Examiner* — Victoria J Hicks
(74) *Attorney, Agent, or Firm* — Schwegman Lundberg & Woessner, P.A.

(57) ABSTRACT

A head and neck covering is cut from a flat sheet of foam material to form a body portion of the head and neck covering. The foam material has a first surface cut to form an eye region, mouth region and neck region. The foam material has a second surface opposite the first surface which is continuous other than an opening for intubation. The foam material is compliant so that the body portion conforms to contours of the head and neck of the anesthetized patient. A closure mechanism is attached to the body portion for securing the head and neck covering around the anesthetized patient. The foam material reduces a potential for trauma to the head and neck of the anesthetized patient. A plurality of channels is formed in the foam material. Warm fluid is circulated through the channels to reduce heat loss for the patient.

25 Claims, 10 Drawing Sheets

(51) Int. Cl.
  *A61F 7/02* (2006.01)
  *A61F 13/12* (2006.01)
  *A61B 46/00* (2016.01)
  *A61F 7/00* (2006.01)
  *A61G 13/12* (2006.01)
  *A61B 46/23* (2016.01)

(52) U.S. Cl.
  CPC ............ *A61F 13/122* (2013.01); *A61B 46/40* (2016.02); *A61B 2046/234* (2016.02); *A61F 2007/0002* (2013.01); *A61F 2007/0054* (2013.01); *A61G 13/121* (2013.01); *Y10T 29/49826* (2015.01)

(58) Field of Classification Search
  CPC ...... A61F 2007/0004; A61F 2007/0005; A61F 2007/0006; A61F 2007/0007; A61F 2007/0008; A61F 2007/0009; A61F 2007/0013; A61F 2007/0014; A61F 2007/0015; A61F 2007/0017
  USPC ......... 128/857, 846, 201.22, 201.33, 201.25, 128/201.26, 205.12; 607/104, 109; 5/638; 2/171, 173, 174, 9; 132/319, 333
  See application file for complete search history.

(56) References Cited

U.S. PATENT DOCUMENTS

| | | | |
|---|---|---|---|
| 4,572,173 | A | 2/1986 | Comeau |
| 5,228,431 | A | 7/1993 | Giarretto |
| 5,310,400 | A * | 5/1994 | Rogers et al. .................... 602/5 |
| 5,370,110 | A | 12/1994 | Corn |
| 5,643,336 | A * | 7/1997 | Lopez-Claros ............... 607/104 |
| 5,706,828 | A * | 1/1998 | Shiota ........................... 128/857 |
| 5,865,196 | A * | 2/1999 | Foote ............................ 132/319 |
| 6,112,333 | A | 9/2000 | Mazzei |
| 6,490,737 | B1 * | 12/2002 | Mazzei et al. .................... 2/410 |
| 6,854,128 | B1 | 2/2005 | Faulk |
| 7,296,570 | B2 * | 11/2007 | Hutchinson .............. 128/201.26 |
| 2003/0182706 | A1 | 10/2003 | Williams |
| 2006/0037608 | A1 | 2/2006 | Silva et al. |
| 2008/0201827 | A1 | 8/2008 | Hipps |

* cited by examiner

PROTECTIVE HEAD COVERING WITH NECK SUPPORT FOR ANESTHETIZED PATIENT AND METHOD THEREFOR

FIELD OF THE INVENTION

The present invention relates in general to medical devices and, more particularly, to a protective head covering with neck support for an anesthetized patient.

BACKGROUND OF THE INVENTION

People routinely undergo surgery for treatment of a variety of medical conditions. In many cases, the patients are placed under general anesthesia for the surgical procedure. While under general anesthesia, the patient is unconscious and cannot respond or react to external stimuli or conditions. In some surgical procedures, there is a potential for these external conditions to cause trauma to the patient. For example, during certain orthopaedic surgical procedures, the surgeon must exert considerable pressure on various parts of the body, e.g., to the arms, legs, shoulder, and torso. In addition, the surgeon uses a variety of instruments during the procedure. The pressure on the body and use of surgical instruments create the potential for unintentional trauma to the patient, particularly to the head, face, ears, eyes, and neck area. The patient may receive pressure marks or sores from direct contact with surgical instruments and body positioning techniques. Any pressure applied to the ocular structures, even a short time, can cause damage or blindness to the eye. The body is typically covered at most by a blanket or cloth, which provides minimal protection.

Another challenge is the task of rolling the patient over from a supine position to a prone position on the operating table or from a cart onto the operating table. Depending on the procedure, the patient may be intubated, which creates a risk of neck injury during the roll-over process. After the procedure, the patient must again be rolled off the operating table onto a gurney. Still anesthetized, the risk of neck injury is again present if the head is not properly supported and manipulated during patient movement.

If an emergency develops while the patient is in the prone position, requiring the patient to be rolled to the supine position, valuable time can be lost trying to properly support the patient without injury to the neck, and without crimping the airway supply tubing and monitoring equipment communicating through the nose and mouth of the patient.

One approach found in U.S. Pat. No. 6,490,737 involves a molded helmet, which partially covers the patient's face and head. The helmet is particularly designed for procedures with the patient in the prone position and, in fact, the helmet can be rigidly mounted to the operating table, as shown in FIG. 8 of U.S. Pat. No. 6,490,737. However, in the prone position, the forehead and chin areas are exposed to continuous pressure by the weight of the patient's own head. If not relieved by regular movement of the face to allow blood flow, the pressure can cause localized ischemia to the chin and forehead area. In addition, the helmet leaves the eyes, cheeks, nose, and back of the head exposed and vulnerable to objects smaller than the openings in the helmet. The helmet is molded to a rigid form factor so the head is likely to shift in position relative to the helmet.

In the anesthetized state, the patient is unable to respond or react to any of these conditions. The surgeon, anesthesiologist, and surgical staff must be constantly aware of patient safety to avoid unnecessary trauma.

The operating room is typically maintained at a low temperature, in part for the comfort and alertness of the surgical team. The patient may experience body heat loss in the low temperature environment. The torso and upper and lower extremities are typically covered by a blanket for warmth. However, a significant amount of heat can be lost passively through the head and neck. A surgical cap can reduce some heat loss, but typically does not cover the face and certainly does not remove the potential for injury.

SUMMARY OF THE INVENTION

A need exists to protect the head and neck of the patient from external conditions to avoid unnecessary trauma. Accordingly, in one embodiment, the present invention is a head and neck covering for an anesthetized patient comprising a flat sheet of foam material cut to form a body portion of the head and neck covering. The foam material has a first surface cut to form an eye region, mouth region, and neck region. The foam material has a second surface opposite the first surface, which is continuous other than an opening for intubation. The foam material is compliant so that the body portion conforms to contours of the head and neck of the anesthetized patient. A closure mechanism is attached to the body portion for securing the head and neck covering around the anesthetized patient.

In another embodiment, the present invention is a head covering for an anesthetized patient comprising a flat sheet of foam material cut to form a body portion of the head covering. The foam material has a first surface cut to form an eye region and mouth region. The foam material has a second surface opposite the first surface which is continuous. A closure mechanism is attached to the body portion for securing the head covering around the anesthetized patient.

In another embodiment, the present invention is a head covering for an anesthetized patient comprising a foam material having a first surface cut to form an eye region and mouth region. The foam material has a second surface opposite the first surface which is continuous. An elastic material is integrated with the foam material for securing the head covering around the anesthetized patient.

In another embodiment, the present invention is a method of making a head and neck covering for an anesthetized patient comprising the steps of providing a flat sheet of foam material, and cutting the foam material to form a body portion of the head and neck covering. The foam material has a first surface cut to form an eye region, mouth region and neck region. The foam material has a second surface opposite the first surface which is continuous other than an opening for intubation. The method further includes the step of attaching a closure mechanism to the body portion for securing the head and neck covering around the anesthetized patient.

In another embodiment, the present invention is a method of making a head covering for an anesthetized patient comprising the steps of providing a flat sheet of foam material, and cutting the foam material to form a body portion of the head covering. The foam material has a first surface cut to form an eye region and mouth region. The foam material has a second surface opposite the first surface which is continuous. The method further includes the step of attaching a closure mechanism to the body portion for securing the head covering around the anesthetized patient.

DETAILED DESCRIPTION OF THE DRAWINGS

The present invention is described in one or more embodiments in the following description with reference to the figures, in which like numerals represent the same or similar elements. While the invention is described in terms of the best mode for achieving the invention's objectives, it will be appreciated by those skilled in the art that it is intended to cover alternatives, modifications, and equivalents as may be included within the spirit and scope of the invention as defined by the appended claims and their equivalents as supported by the following disclosure and drawings.

Figure 1:
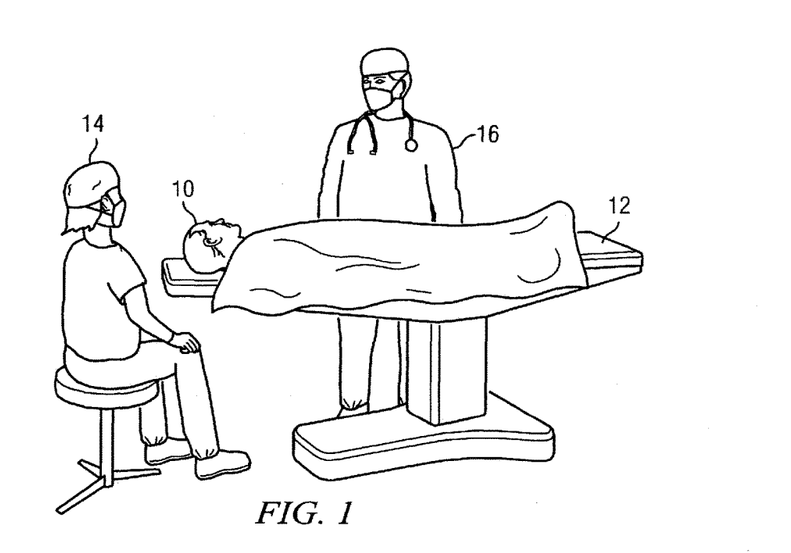
FIG. 1 illustrates a patient in supine position for surgery.

In FIG. 1, patient 10 is shown in a supine position on operating table 12. Anesthesiologist 14 places patient 10 under general anesthesia in preparation for surgery. In the anesthetized state, patient 10 is unconscious and cannot respond or react to external stimuli or conditions. Surgeon 16 performs the surgical procedure on patient 10. In some surgical procedures, such as orthopaedic procedures, surgeon 16 must exert considerable pressure on various parts of the body, e.g., to the arms, legs, shoulder, and torso. In addition, surgeon 16 uses a variety of instruments during the procedure. The pressure on the body and use of surgical instruments create the potential for unintentional trauma to the patient, particularly to the head, face, ears, eyes, and neck area.

Figures 2, 3:
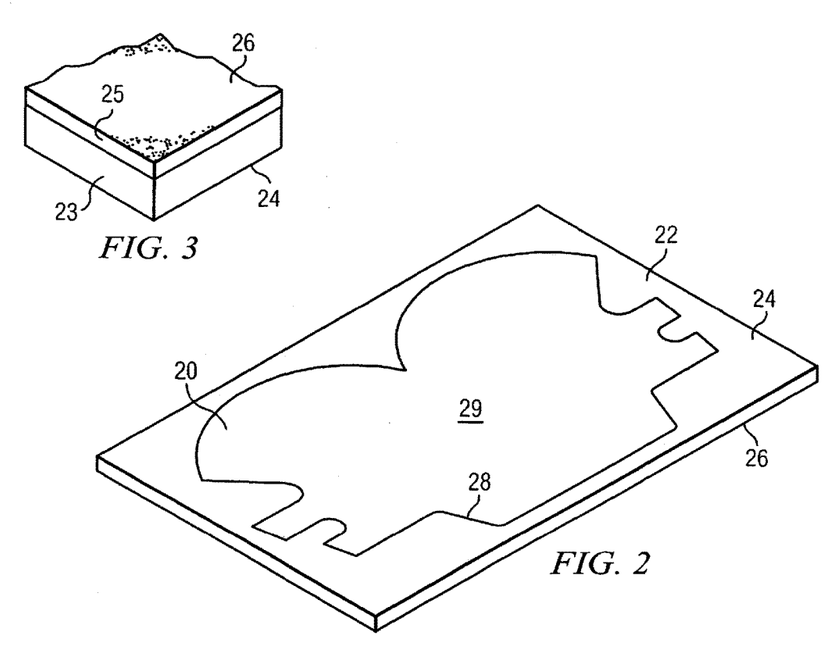
FIG. 2 illustrates a flat sheet of foam material which is cut to a body of a head covering with neck support.
FIG. 3 shows the foam material with an outer impact resistant layer and inner conforming layer.

FIG. 2 shows a protective head covering 20 formed from a flat sheet of medical grade open-cell or closed-cell foam material 22 having sufficient density and thickness to absorb or cushion external forces, e.g., medical instruments and human induced pressure points. Head covering 20 isolates the head and neck of patient 10 from iatrogenic trauma. In particular, head covering 20 protects the eyes, ears, nose, mouth, cheeks, chin, forehead, back, top and sides of the head, and other facial epidermis of patient 10. In one embodiment, foam material 22 has a thickness ranging from 10-30 millimeters (mm). Foam material 22 is compliant and readily conforms to the contour of the head and neck of patient 10. Foam material 22 is waterproof and disposable.

Foam material 22 has an inside surface 24 for epidermis contact, and outside surface 26 opposite surface 24. The surfaces 24-26 of foam material 22 can be treated with a secondary material, such as cloth, neoprene, or silicone, to prevent allergic reactions and improve handling and application of head covering 20. FIG. 3 shows foam material 22 as having multiple layers laminated or joined to create the desired protective and compliant properties. Each layer of foam material 22 can have a different density. The innermost layer 23 adjacent to the face of patient 10 may be soft and conforming, while the outermost layer 25 has sufficient density to protect against impact or pressure.

Figure 4A:
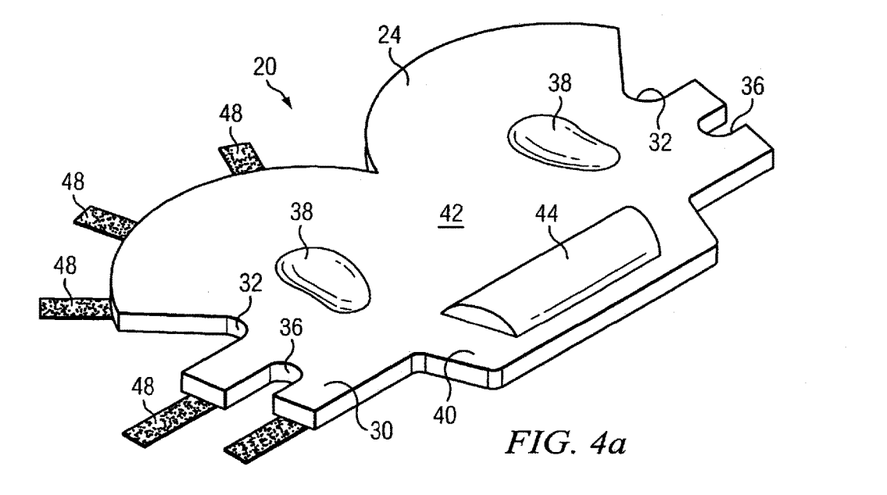
FIGS. 4a-4b illustrate opposite surfaces of the head covering with neck support and locking straps.
Figure 4B:
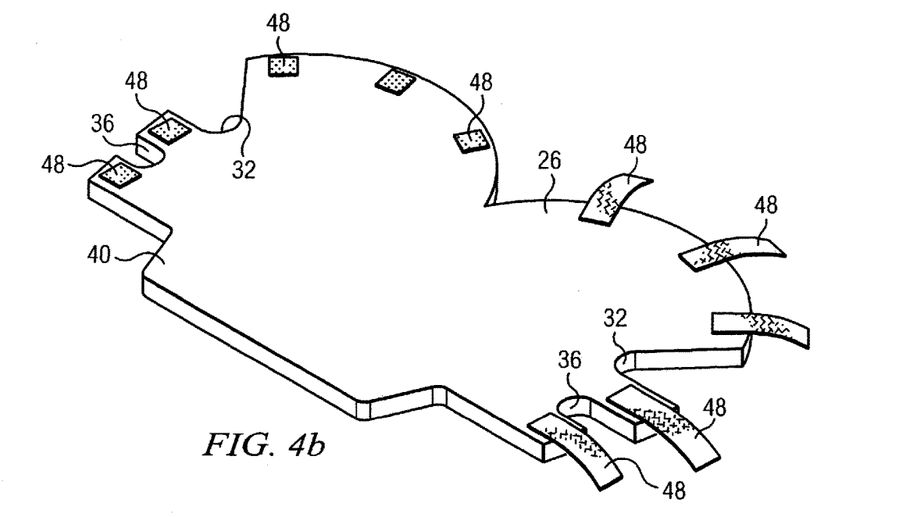

The sheet of foam material 22 is cut along lines 28 with a laser, water cutting jet, hot-knife, stamping, die cutting, or other tool to produce body portion 29 having shape and dimensions necessary to conform to the head and neck of patient 10. In particular, portions of foam material 22 are retained or removed from body portion 29 by the cutting process to form facial region 30, recessed eye and nose region 32, recessed mouth region 36, recessed ear region 38, neck region 40, and back of head region 42, as shown in FIG. 4a. Neck region 40 has padding 44 for additional neck support. FIG. 4b shows outside surface 26 of head covering 20. After the cutting process, a plurality of closure mechanisms 48, e.g., straps, Velcro, laces, and fasteners, can be attached around a perimeter of foam material 22 in appropriate locations to secure head covering 20 to the head and neck of patient 10.

Figure 5A:
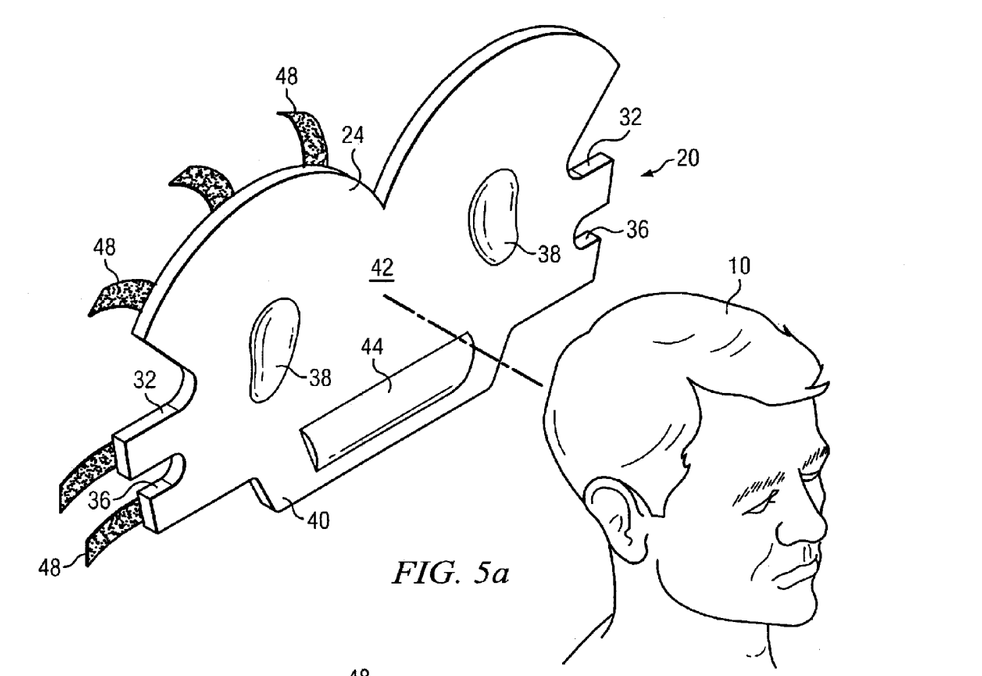
FIGS. 5a-5b illustrate the head covering affixed to the patient.
Figure 5B:
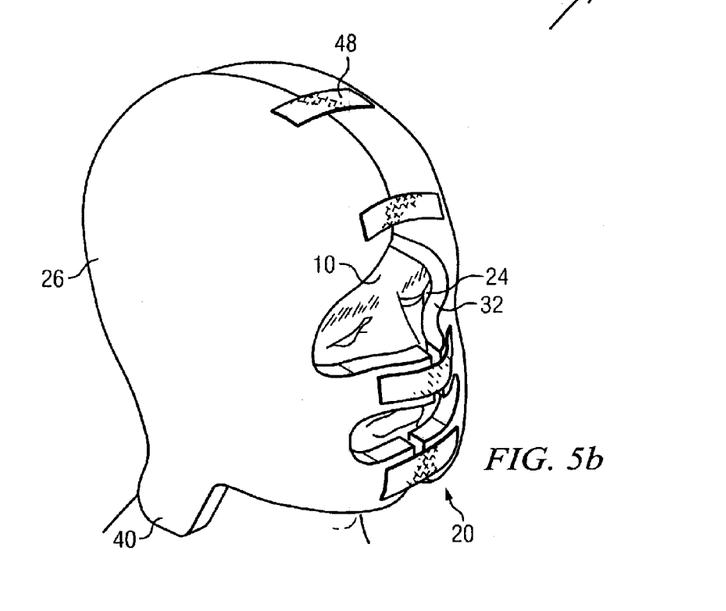

In one application, as shown in FIG. 5a, surface 24 of region 42 is brought into contact with the back of the head of patient 10 so that region 40 is disposed over the neck of the patient. Head covering 20 is wrapped around the front of the head and neck of patient 10 and closure mechanism 48 is secured so that the patient's eyes and nose are centered under recessed region 32, the patient's mouth is centered under recessed region 36, and the patient's ears are centered under recessed region 38, as shown in FIG. 5b. The compliant property of head covering 20 causes surface 24 to conform to the contours of the head, face, and neck of patent 10. Once secured in place with closure mechanism 48, head covering 20 is unlikely to shift due to the continuous and substantial contact between surface 24 and the head and face of patient 10.

The flat sheet of foam material 20 has advantages over the molded helmet, as found in the prior art. The flat nature of sheet 22 is less costly to manufacture and more convenient to package for shipment and storage. Head covering 20 is compliant and readily conforms around most head dimensions, i.e., one size fits all. Once applied, head covering 20 is less likely to shift in position.

Figure 6A:
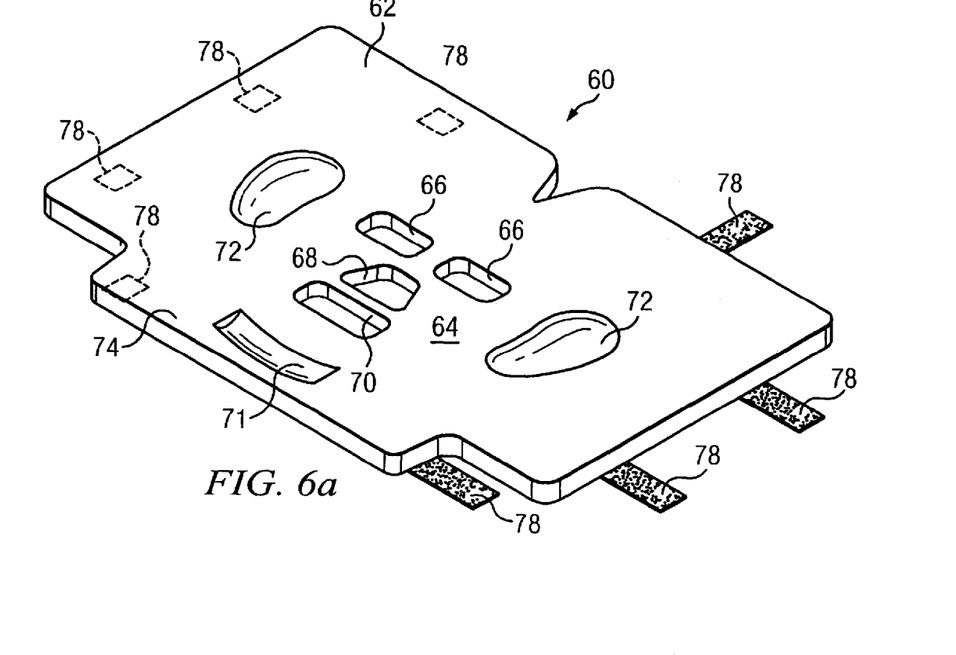
FIGS. 6a-6b illustrate opposite surfaces of another embodiment of the head covering with neck support and locking straps.

FIG. 6a shows another embodiment of the protective head covering. Head covering 60 is formed from a flat sheet of medical grade open-cell or closed-cell foam material having sufficient density and thickness to absorb or cushion external forces, e.g., medical instruments and human induced pressure points. Head covering 60 isolates the head and neck of patient 10 from iatrogenic trauma. In particular, head covering 60 protects the eyes, ears, nose, mouth, cheeks, chin, forehead, back, top and sides of the head, and other facial epidermis of patient 10. In one embodiment, the foam material has a thickness ranging from 10-30 mm. The foam material is compliant and readily conforms to the contour of the head and neck of patient 10. The foam material is waterproof and disposable.

Figure 6B:
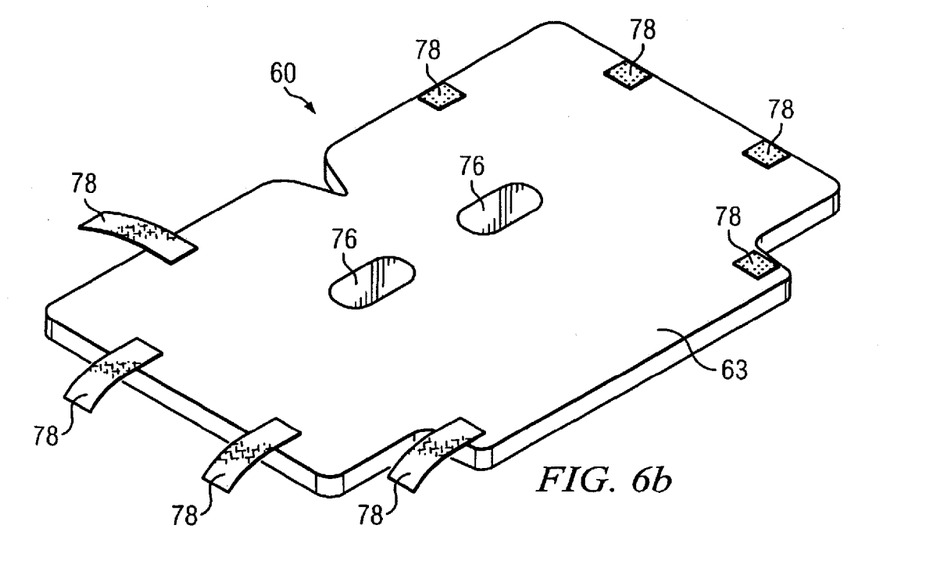

The foam material has an inside surface 62 for epidermis contact. FIG. 6b shows outside surface 63, opposite surface 62. The surfaces 62 and 63 of the foam material can be treated with a secondary material, such as cloth, neoprene, or silicone, to prevent allergic reactions and improve handling and application of head covering 60. The foam material may have multiple layers laminated or joined to create the desired protective and compliant properties. For example, the innermost layer adjacent to the face of patient 10 may be soft and conforming, while the outermost layer has sufficient density to protect against impact or pressure. Regions 76 of surface 63 are clear or opaque to enable observation of the eyes of patient 10 which aids in alignment of head covering 60.

Head covering 60 has facial region 64, recessed eye region 66, recessed nose region 68, recessed mouth region 70, chin region 71, recessed ear region 72, and neck region 74. Any external pressure or force applied to surface 63 is distributed over an area to avoid injury to any specific body part. The recessed regions provide spacing to avoid direct contact or pressure on the eye, noise, mouth, etc. A plurality of closure mechanisms 78, e.g., straps, Velcro, laces, and fasteners, can be attached around a perimeter of the foam material in appropriate locations to secure head covering 60 to the head and neck of patient 10.

Figure 7A:
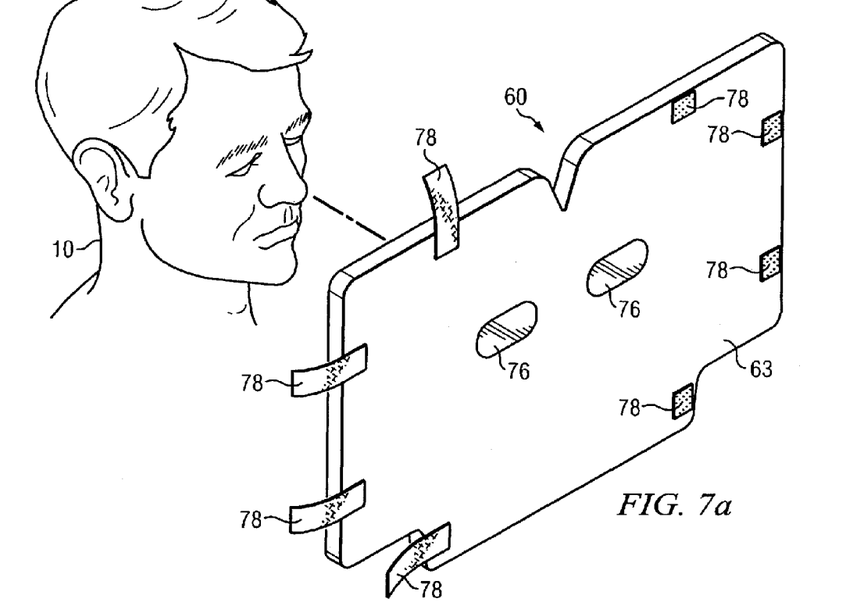
FIGS. 7a-7b illustrate the head covering of FIGS. 5a-5b affixed to the patient.
Figure 7B:
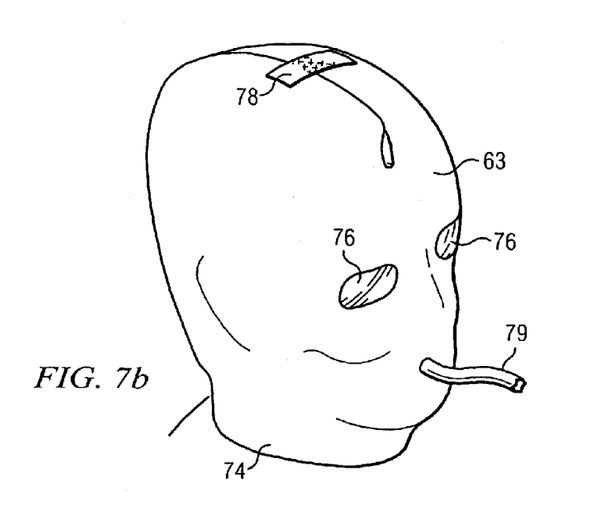

In one application, as shown in FIG. 7a, surface 62 of region 64 is brought into contact with the face of patient 10 so that region 74 is disposed over the neck of the patient. Head covering 60 is wrapped around the back of the head and neck of patient 10 and closure mechanism 78 is secured so that the patient's eyes are centered under recessed region 66, the patient's nose is centered over recessed region 68, the patient's mouth is centered under recessed region 70, the patient's chin is aligned with region 71, and the patient's ears are centered under recessed region 72, as shown in FIG. 7b. The compliant property of head covering 60 causes surface 62 to conform to the contours of the head, face, and neck of patient 10. Once secured in place with closure mechanism 78, head covering 60 is unlikely to shift due to the continuous contact between surface 62 and the head and face of patient 10. The outside surface 63 can be continuous other than an opening for intubation tube 79 to the air passage of patient 10. Therefore, all areas of the patient's head and neck are isolated from external conditions to reduce the risk of trauma.

Figure 8A:
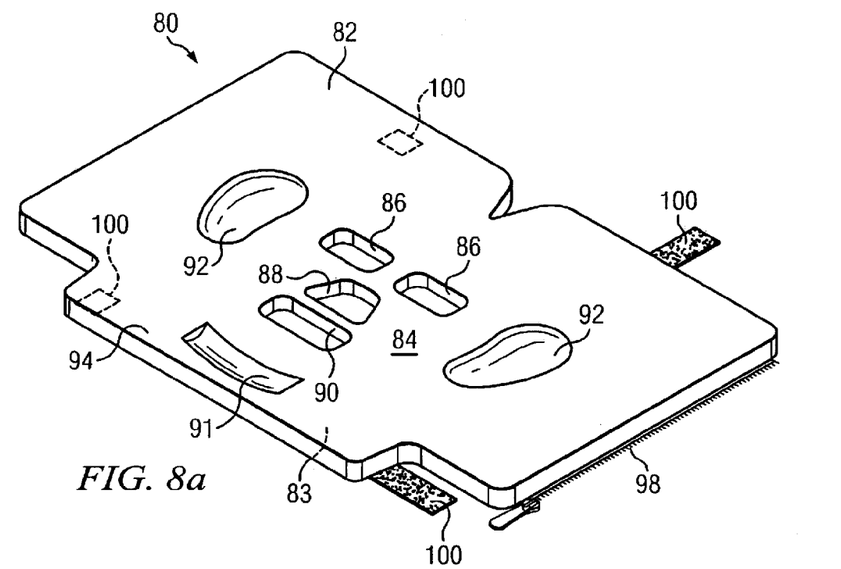
FIGS. 8a-8b illustrate opposite surfaces of another embodiment of the head covering with neck support and locking Velcro strips.

FIG. 8a shows another embodiment of the protective head covering. Head covering 80 is formed from a flat sheet of medical grade open-cell or closed-cell foam material having sufficient density and thickness to absorb or cushion external forces, e.g., medical instruments and human induced pressure points. Head covering 80 isolates the head and neck of patient 10 from iatrogenic trauma. In particular, head covering 80 protects the eyes, ears, nose, mouth, cheeks, chin, forehead, back, top and sides of the head, and other facial epidermis of patient 10. In one embodiment, the foam material has a thickness ranging from 10-30 mm. The foam material is compliant and readily conforms to the contour of the head and neck of patient 10. The foam material is waterproof and disposable.

Figure 8B:
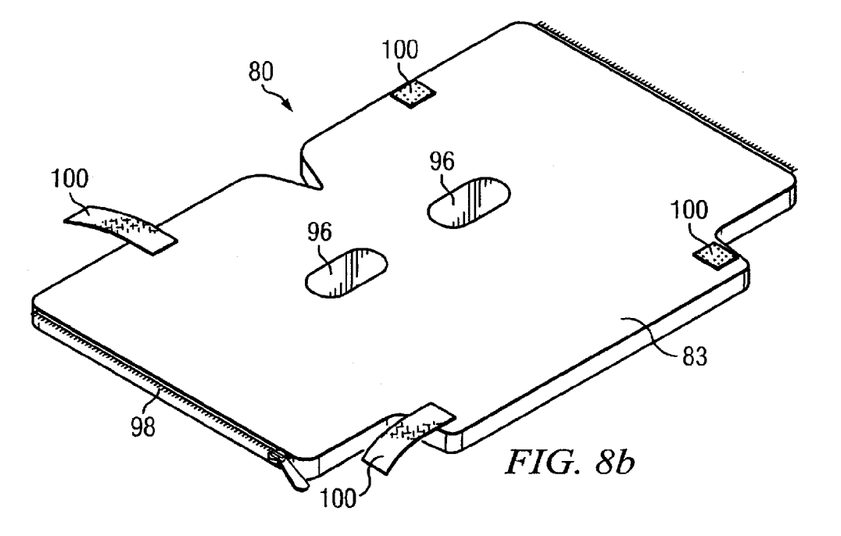

The foam material has an inside surface 82 for epidermis contact. FIG. 8b shows outside surface 83, opposite surface 82. The surfaces 82 and 83 of the foam material can be treated with a secondary material, such as cloth, neoprene, or silicone, to prevent allergic reactions and improve handling and application of head covering 80. The foam material may have multiple layers laminated or joined to create the desired protective and compliant properties. For example, the innermost layer adjacent to the face of patient 10 may be soft and conforming, while the outermost layer has sufficient density to protect against impact or pressure.

Regions 96 of surface 83 are clear or opaque to enable observation of the eyes of patient 10 which aids in alignment of head covering 80.

Head covering 80 has facial region 84, recessed eye region 86, recessed nose region 88, recessed mouth region 90, recessed chin region 91, recessed ear region 92, and recessed neck region 94. Any external pressure or force applied to surface 83 is distributed over an area to avoid injury to any specific body part. The recessed regions provide spacing to avoid direct contact or pressure on the eye, noise, mouth, etc. A metal or plastic zipper 98 and closure mechanism 100 is attached to secure head covering 80 to the head and neck of patient 10.

Figure 9:
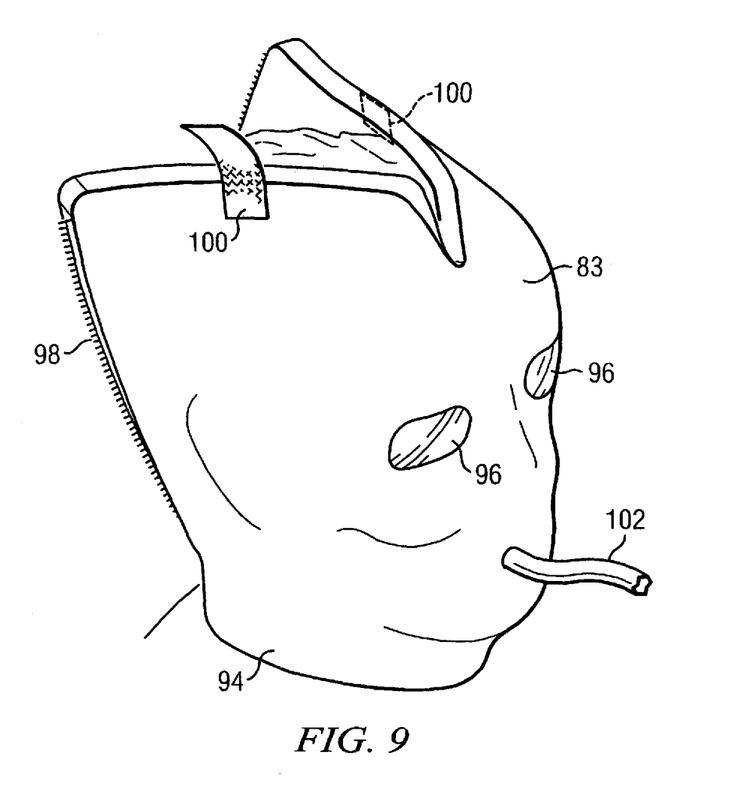
FIG. 9 illustrates the head covering of FIGS. 7a-7b affixed to the patient.

In one application, as shown in FIG. 9, surface 84 of region 82 is brought into contact with the face of patient 10 so that region 94 is disposed over the neck of the patient. Head covering 80 is wrapped around the back of the head and neck of patient 10 and zipper 98 and closure mechanism 100 are closed so that the patient's eyes are centered under region 86, the patient's nose is centered over region 88, the patient's mouth is centered under region 90, the patient's chin is aligned with recessed region 91, and the patient's ears are centered under region 92. The compliant property of head covering 80 causes surface 82 to conform to the contours of the head, face, and neck of patent 10. Once secured in place with zipper 98 and closure mechanism 100, head covering 80 is unlikely to shift due to the continuous contact between surface 82 and the head and face of patient 10. The outside surface 83 can be continuous other than an opening for intubation tube 102 to the air passage of patient 10. Therefore, all areas of the patient's head and neck are isolated from external conditions to reduce the risk of trauma.

Figure 10A:
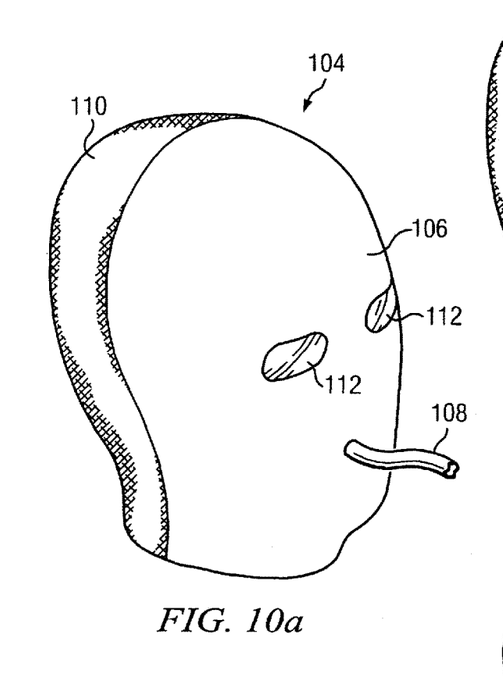
FIGS. 10a-10b illustrate another embodiment of the head covering.
Figure 10B:
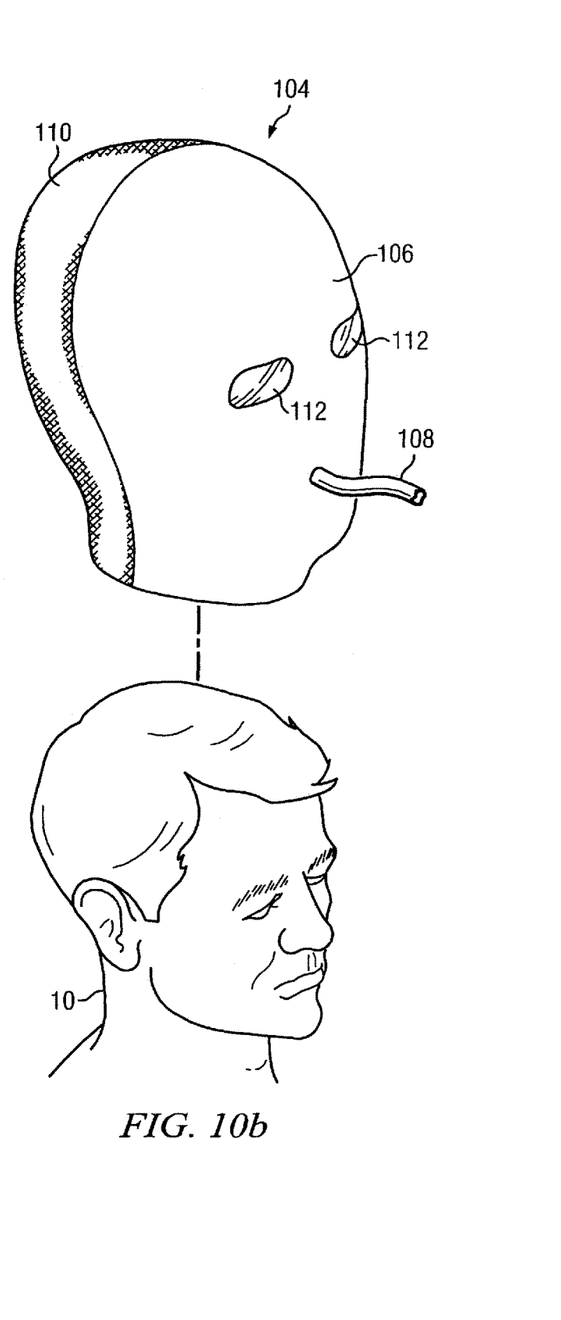

FIG. 10a shows another embodiment of the protective head covering. In this case, head covering 104 is formed as a tube or hood having a surface 106 made from medical grade open-cell or closed-cell foam material having sufficient density and thickness to absorb or cushion external forces, e.g., medical instruments and human induced pressure points. The surface 106 is continuous other than an opening for intubation tube 108 to the air passage of patient 10. Region 110 is stretchable or mesh material, such as spandex, elastane, or other synthetic fiber or fabric made from a polymer containing polyurethane. Stretchable material 110 is integrated with surface 106 to allow head covering 104 to be fitted over the head of patient 10, as shown in FIG. 10b. Head covering 104 isolates the head and neck of patient 10 from iatrogenic trauma. In particular, head covering 104 protects the eyes, ears, nose, mouth, cheeks, chin, forehead, back, top and sides of the head, and other facial epidermis of patient 10. The foam material is compliant and readily conforms to the contour of the head and neck of patient 10. The foam material is waterproof and disposable.

Figure 11:
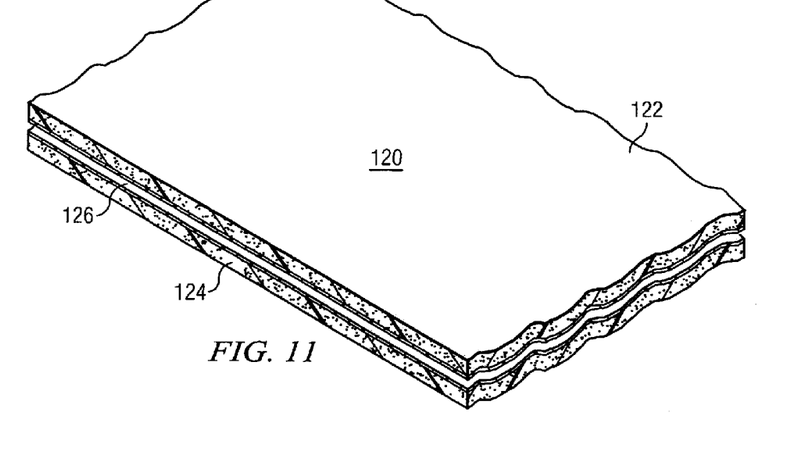
FIG. 11 illustrates the foam material with air bladder.

The foam material has an inside surface for epidermis contact and an outside surface for protection, similar to FIGS. 8a-8b. FIG. 11 shows another embodiment with foam material 120 having outer surface 122 and inner surface 124. An air bladder or cavity 126 is disposed between outer surface 122 and inner surface 124. By pumping air or fluid into bladder 126, the inner surface 124 is pressed against the head and neck of patient 10 to provide a conformal fit, as shown in FIGS. 7b, 9, and 10b.

Figure 12:
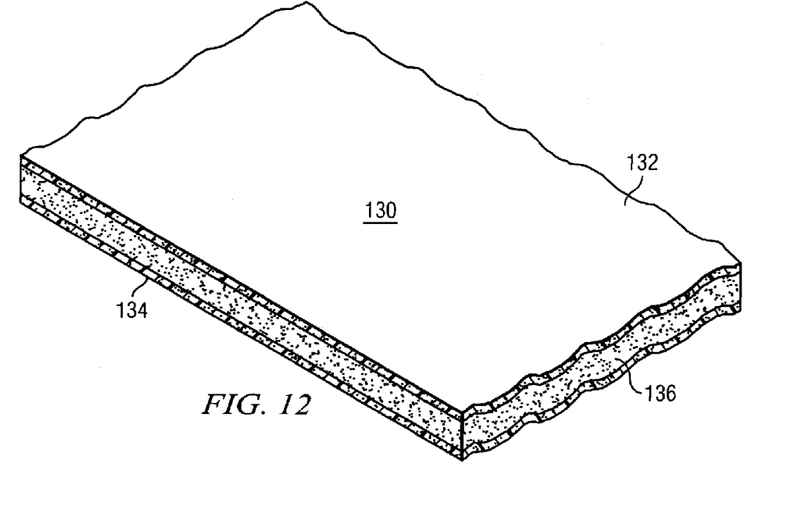
FIG. 12 illustrates the foam material with intermediate expandable material.

In another embodiment shown in FIG. 12, foam material 130 has multiple layers laminated or joined to create the desired protective and compliant properties. For example, the outermost layer 132 is a dense material to protect against impact or pressure. The innermost layer 134 is soft and conforming to the contour of the head and neck of patient 10. An intermediate layer 136 contains a memory cell material which expands with introduction of air or fluid. The inner surface 134 is pressed against the head and neck of patient 10 to provide a conformal fit. Any external pressure or force applied to surface 132 is distributed over an area to avoid injury to any specific body part.

Figure 13:
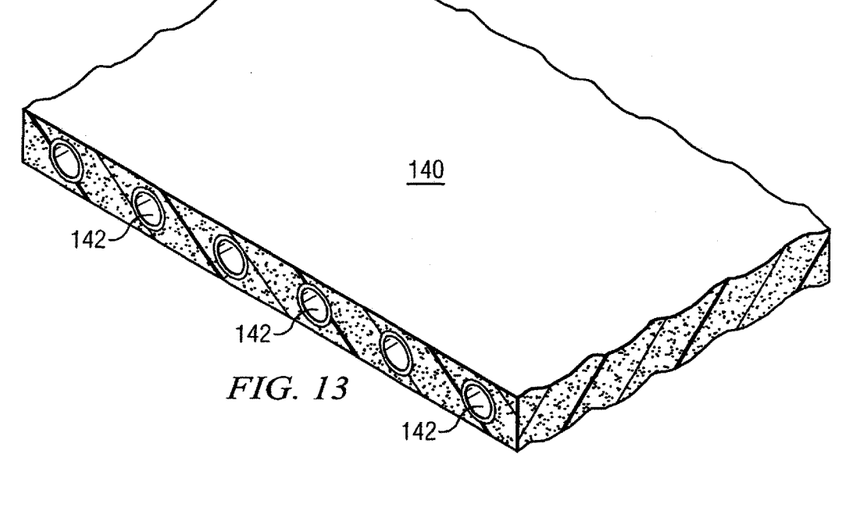
FIG. 13 illustrates the foam material with channels for circulating heated fluid to reduce body heat loss.
Figure 14:
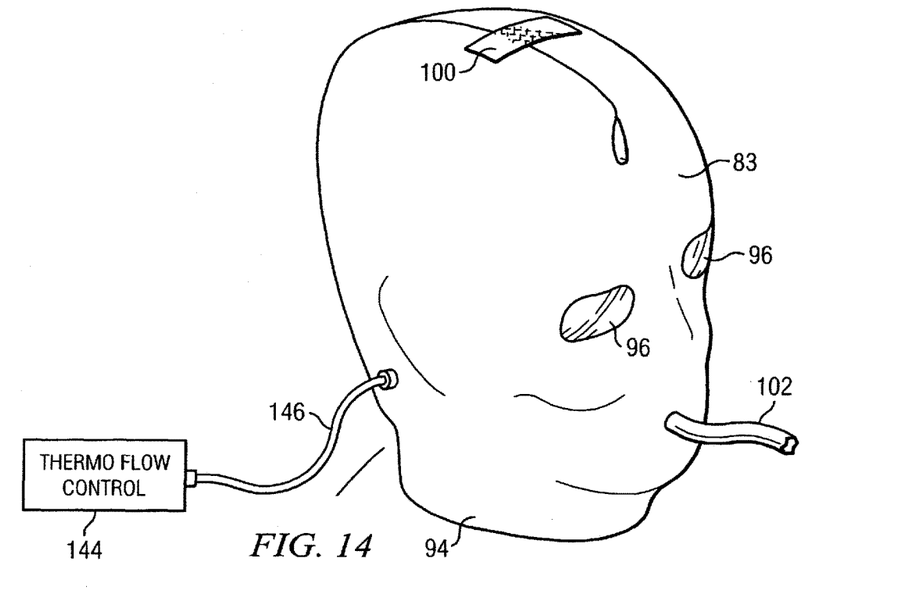
FIG. 14 illustrates a thermal flow controller for circulating heated fluid to the channels in the foam material.

The operating room is typically maintained at a low temperature, e.g., 20-24° C., in part for the comfort and alertness of the surgical team. The patient may experience body heat loss and become hypothermic in the low temperature environment. To minimize heat loss through the head and face during medical procedures, the head covering is made with foam material 140 containing a plurality of channels or tubing 142, as shown in FIG. 13. Warm fluid is circulated through channels 142 to transfer heat to patient 10. For example, thermal flow control 144 circulates heated fluid through tube 146 and channels 142, as shown in FIG. 14. The warm fluid minimizes heat loss and provides comfort for patient 10 in the post anesthesia care unit (PACU), decreases chance of infection, improves blood clotting, and reduces blood loss.

While one or more embodiments of the present invention have been illustrated in detail, the skilled artisan will appreciate that modifications and adaptations to those embodiments may be made without departing from the scope of the present invention as set forth in the following claims.

What is claimed:

1. An apparatus configured to form a head covering for an anesthetized patient, the apparatus comprising:
   compliant foam material that is conformable to contours of a head of the anesthetized patient, the foam material cut to form a body portion of the head covering, the foam material including an inner layer for positioning against the anesthetized patient's face, the inner layer having a first density, and the foam material including an outer layer having a different second density, the inner layer corresponding to a first surface of the foam material and the outer layer corresponding to an opposite second; surface of the foam material;
   an eye recess that extends through the first surface and through at least a portion of the inner layer of the foam material without extending through the opposite second surface of the foam material, the eye recess configured to correspond to an eye region of the anesthetized patient;
   a mouth recess that extends through the first surface and through at least a portion of the inner layer of the foam material without extending through the opposite second surface of the foam material, the mouth recess configured to correspond to a mouth region of the anesthetized patient; and
   a closure mechanism attached to the foam material for securing the apparatus about the head of the anesthetized patient.

2. The apparatus of claim 1, further including an air bladder disposed between the first and second surfaces of the foam material.

3. The apparatus of claim 1, wherein the foam material has a thickness of 10-30 millimeters.

4. The apparatus of claim 1, further including a secondary material placed over the foam material, the secondary material selected from the group consisting of cloth, neoprene, and silicone.

5. The apparatus of claim 1, wherein the closure mechanism includes a strap, fastener, or zipper.

6. The apparatus of claim 1, further including:
   a plurality of channels formed in the foam material; and
   a thermal flow control for circulating fluid through the channels formed in the foam material.

7. The apparatus of claim 1, further including an intermediate expandable layer between the first and opposite second surfaces of the foam material.

8. A head covering for an anesthetized patient, the head covering comprising:
   foam material, cut from a flat sheet of compliant foam material, and configured to form a body portion of the head covering, the foam material including a conforming inner layer having a first density for positioning against the anesthetized patient's face and including an outer layer having a different second density and the outer layer being configured to protect the anesthetized patient against impact or pressure, the foam material including a first surface and an opposite second surface;
   a recessed eye region for positioning at a corresponding eye region of the anesthetized patient, the recessed eye region including a recess formed through the first surface and into the inner layer of the foam material, and the recessed eye region covered by the opposite second surface of the foam material; and
   a recessed mouth region for positioning at a corresponding mouth region of the anesthetized patient, the recessed mouth region including a recess formed through the first surface and into the inner layer of the foam material, and the recessed mouth region covered by the opposite second surface of the foam material.

9. The head covering of claim 8, wherein the foam material is compliant so that the body portion is capable of conforming to contours of a head of the anesthetized patient.

10. The head covering of claim 8, further including an air bladder disposed between the first and opposite second surfaces of the foam material.

11. The head covering of claim 8, further including:
    a plurality of channels formed in the foam material; and
    a thermal flow control for circulating fluid through the channels formed in the foam material.

12. A head covering hood for an anesthetized patient, the head covering hood having a neck opening that is configured to be pulled over the patient's head to place the head covering hood on the patient, the head covering hood comprising:
    a foam material having a first surface, configured for contacting a face of the anesthetized patient when the head covering is worn by the patient, and an opposite second surface, the foam material further including:
      a recessed eye region including a pair of eye recesses positioned to respectively correspond with eyes of the anesthetized patient when the head covering hood is worn by the patient, the pair of eye recesses formed through the first surface of the foam material and covered by the opposite second surface of the foam material;
      an opening for intubation positioned to correspond with a mouth of the anesthetized patient when the head covering hood is worn by the patient; and
    an elastic material coupled continuously along an outer perimeter of the foam material and configured to secure the head covering hood about top and rear portions of the head of the anesthetized patient.

13. The head covering of claim 12, wherein the foam material is compliant so that the head covering is capable of conforming to contours of a head of the anesthetized patient.

14. The head covering of claim 12, further including an air bladder disposed between the first and second surfaces of the foam material.

15. The head covering of claim 12, further including:
a plurality of channels formed in the foam material; and
a thermal flow control for circulating fluid through the channels formed in the foam material.

16. A method of making a head covering for an anesthetized patient, the method comprising:
providing a flat sheet of foam material, the foam material including a conforming inner layer having a first density for positioning against the anesthetized patient's face and including an outer layer having a different second density and the outer layer being configured to protect the anesthetized patient against impact or pressure, the foam material including a first surface and an opposite second surface;
cutting the foam material to form a body portion of the head covering;
removing a portion of the inner layer of the foam material from a first surface of the foam material to form multiple recesses that extend only partially through the foam material without extending through the opposite second surface, the multiple recesses including a recessed eye region, and a recessed mouth region; and
attaching a closure mechanism to the second surface of the foam material for securing the head covering around the head of the anesthetized patient.

17. The method of claim 16, wherein the foam material is compliant so that the body portion is capable of conforming to contours of a head of the anesthetized patient.

18. The method of claim 16, wherein the closure mechanism includes a strap, fastener, or zipper.

19. The method of claim 16, further including:
forming a plurality of channels in the foam material, the plurality of channels configured to circulate a fluid.

20. A method of making a head covering for an anesthetized patient, comprising:
providing a flat sheet of foam material, the foam material having a first surface and an opposite second surface, and the flat sheet of foam material having a side extending around its periphery;
cutting into the foam material and through the first and opposite second surfaces of the foam material to remove selected portions of the foam material and to thereby form a body portion of the head covering, the body portion including, in each of two opposite sides of the cut foam material, respective halves of each of an eye and nose region and a separate mouth region;
cutting the first surface of the foam material to form an ear region that does not extend through the second surface of the foam material;
providing padding in a neck region of the body portion of the head covering, the neck region corresponding to a rear neck area of the anesthetized patient when the head covering is worn by the anesthetized patient; and
attaching closure mechanisms to the second surface of the foam material adjacent to the eye and nose region and adjacent to the mouth region, the closure mechanisms configured to be joined in front of the patient's face for securing the head covering around the anesthetized patient's head.

21. The method of claim 20, wherein the foam material is compliant so that the body portion is capable of conforming to contours of a head of the anesthetized patient.

22. The method of claim 20, further including disposing an air bladder between the first and second surfaces of the foam material.

23. The method of claim 20, wherein the closure mechanism includes a strap, fastener, or zipper.

24. The method of claim 20, wherein the body portion further includes a neck region for covering the neck of the anesthetized patient.

25. The method of claim 20, further including:
forming a plurality of channels in the foam material, the plurality of channels configured to circulate a fluid.

* * * * *

UNITED STATES PATENT AND TRADEMARK OFFICE
CERTIFICATE OF CORRECTION

PATENT NO.       : 10,092,453 B2
APPLICATION NO.  : 12/539320
DATED            : October 9, 2018
INVENTOR(S)      : Mattalino et al.

It is certified that error appears in the above-identified patent and that said Letters Patent is hereby corrected as shown below:

In the Claims

In Column 7, Line 41, in Claim 1, delete "second;" and insert --second-- therefor Signed and Sealed this
Twenty-eighth Day of May, 2019

Andrei Iancu
*Director of the United States Patent and Trademark Office*